(12) United States Patent
Waziri et al.

(10) Patent No.: US 11,419,536 B2
(45) Date of Patent: Aug. 23, 2022

(54) METHODS FOR RECORDING SUBGALEAL BRAIN SIGNALS

(71) Applicant: Ice Neurosystems, Inc., Washington, DC (US)

(72) Inventors: Allen Edward Waziri, Washington, DC (US); Ronald G. Emerson, New York, NY (US)

(73) Assignee: Ice Neurosystems, inc., Washington, DC (US)

( * ) Notice: Subject to any disclaimer, the term of this patent is extended or adjusted under 35 U.S.C. 154(b) by 0 days.

(21) Appl. No.: 17/534,854

(22) Filed: Nov. 24, 2021

(65) Prior Publication Data

US 2022/0079494 A1 Mar. 17, 2022

Related U.S. Application Data

(63) Continuation of application No. 17/236,932, filed on Apr. 21, 2021, which is a continuation of application No. PCT/US2019/057247, filed on Oct. 21, 2019.

(60) Provisional application No. 62/748,609, filed on Oct. 22, 2018.

(51) Int. Cl.
*A61B 5/372* (2021.01)
*A61B 5/00* (2006.01)
*A61B 5/293* (2021.01)
*A61B 5/31* (2021.01)

(52) U.S. Cl.
CPC .............. *A61B 5/293* (2021.01); *A61B 5/31* (2021.01); *A61B 5/372* (2021.01); *A61B 5/6848* (2013.01); *A61B 5/6868* (2013.01); *A61B 5/7225* (2013.01); *A61B 2562/063* (2013.01)

(58) Field of Classification Search
CPC combination set(s) only.
See application file for complete search history.

(56) References Cited

U.S. PATENT DOCUMENTS

| 6,024,702 | A | 2/2000 | Iversen | |
|---|---|---|---|---|
| 2007/0112277 | A1 | 5/2007 | Fischer et al. | |
| 2007/0161919 | A1 | 7/2007 | DiLorenzo | |
| 2008/0183097 | A1* | 7/2008 | Leyde | A61B 5/0006 600/545 |
| 2008/0269716 | A1* | 10/2008 | Bonde | A61B 17/3468 607/118 |
| 2012/0071779 | A1* | 3/2012 | Sarkela | A61B 5/7275 600/544 |

(Continued)

OTHER PUBLICATIONS

International Preliminary Report of Patentability dated Oct. 20, 2020 and received in PCT/US2019/057247.

(Continued)

*Primary Examiner* — Etsub D Berhanu
(74) *Attorney, Agent, or Firm* — Bookoff McAndrews, PLLC

(57) ABSTRACT

The invention encompasses systems and methods allowing for minimally invasive insertion and functional optimization of implantable electrode arrays designed for placement within the subgaleal space to record brain electrical activity. The implantable arrays comprise a support structure capable of being implanted in the subgaleal space and comprising at least one reference element; at least one ground element; and one or more recording elements; and wherein said array is capable of detecting and/or transmitting a subgaleal electrical signal.

21 Claims, 15 Drawing Sheets

(56) References Cited

U.S. PATENT DOCUMENTS

| | | | |
|---|---|---|---|
| 2012/0143297 A1* | 6/2012 | Greene | A61N 1/0558 |
| | | | 607/116 |
| 2012/0257339 A1 | 10/2012 | Leyde | |
| 2013/0053722 A1 | 2/2013 | Carlson et al. | |
| 2013/0204122 A1 | 8/2013 | Hendler et al. | |
| 2017/0035316 A1 | 2/2017 | Kuzniecky et al. | |
| 2017/0100580 A1* | 4/2017 | Olson | A61N 1/0531 |
| 2019/0008403 A1* | 1/2019 | Williams | A61N 1/0504 |

OTHER PUBLICATIONS

International Search Report, Written Opinion and Search Strategy dated Jan. 13, 2020 and received in PCT/US2019/057247.

* cited by examiner

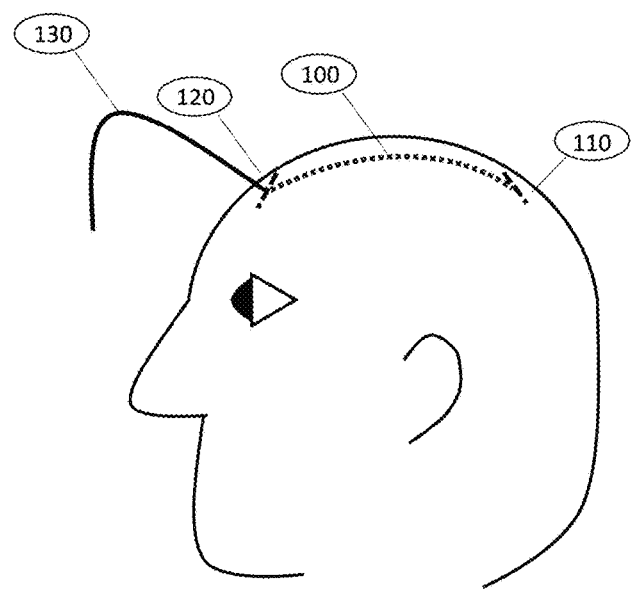
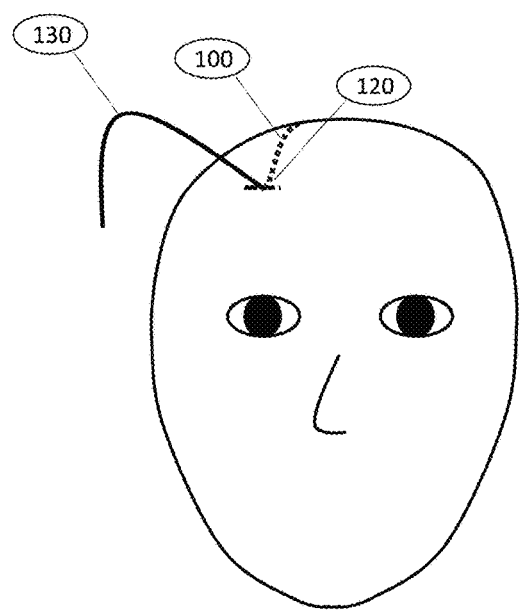
Figure 1A                    Figure 1B

| Recording element number | Channel assignment, bilateral array |
|---|---|
| 1 | Right channel 1 |
| 2 | Right channel 2 |
| 3 | Right channel 3 |
| 4 | Right channel 4 |
| 5 | Right channel 5 |
| 6 | Right channel 6 |
| 7 | Right channel 7 |
| 8 | Right channel 8 |
| 9 | COMMON REFERENCE |
| 10 | GROUND |
| 11 | Left channel 1 |
| 12 | Left channel 2 |
| 13 | Left channel 3 |
| 14 | Left channel 4 |
| 15 | Left channel 5 |
| 16 | Left channel 6 |
| 17 | Left channel 7 |
| 18 | Left channel 8 |
| 19 | COMMON REFERENCE |
| 20 | GROUND |

| Recording element number | Channel assignment, unilateral array |
|---|---|
| 1 | Right channel 1 |
| 2 | Right channel 2 |
| 3 | Right channel 3 |
| 4 | Right channel 4 |
| 5 | COMMON REFERENCE |
| 6 | Right channel 5 |
| 7 | Right channel 6 |
| 8 | Right channel 7 |
| 9 | Right channel 8 |
| 10 | GROUND |

Figure 14

| Right Contact 1 | Right Contact 2 | Right Contact 3 | Right Contact 4 | Left Contact 1 | Left Contact 2 | Left Contact 3 | Left Contact 4 | Primary Synthetic channels removed (right side) | Corresponding synthetic channels removed (left side) | Synthetic channels thus available in balanced montage for comparison |
|---|---|---|---|---|---|---|---|---|---|---|
| Good | Good | Good | Good | Good | Good | Good | Good | None | None | R1-R2, R2-R3, R3-R4, L1-L2, L2-L3, L3-L4 |
| Bad | Good | Good | Good | Good | Good | Good | Good | R1-R2 | L1-L2 | R2-R3, R3-R4, L2-L3, L3-L4 |
| Good | Bad | Good | Good | Good | Good | Good | Good | R1-R2, R2-R3 | L1-L2, L2-L3 | R1-R3, R3-R4, L1-L3, L3-L4 |
| Good | Good | Bad | Good | Good | Good | Good | Good | R2-R3, R3-R4 | L2-L3, L3-L4 | R1-R2, R2-R4, L1-L2, L2-L4 |
| Good | Good | Good | Bad | Good | Good | Good | Good | R3-R4 | L3-L4 | R1-R2, R2-R3, L1-L2, L2-L3 |

METHODS FOR RECORDING SUBGALEAL BRAIN SIGNALS

CROSS-REFERENCE TO RELATED APPLICATIONS

This patent application is a continuation of and claims the benefit of priority to pending U.S. application Ser. No. 17/236,982, filed on Apr. 21, 2021, which is a continuation of PCT/US19/57247, filed Oct. 21, 2019, which claims the benefit of priority from U.S. Provisional Application No. 62/748,609, filed Oct. 22, 2018, all of which are incorporated herein by reference in their entireties.

FIELD OF THE INVENTION

The invention encompasses systems and methods allowing for minimally invasive insertion and functional optimization of electrode arrays designed for temporary placement within the subgaleal space to record brain electrical activity. The described systems and methods allow a health care provider, even without specialized EEG or surgical training, to record and compare clinically relevant bihemispheric high-fidelity EEG signals in the acute setting without the need for application of scalp electrodes or implantation of recording electrodes in a formal surgical setting.

DISCUSSION OF THE RELATED ART

In the following discussion, certain articles and methods will be described for background and introductory purposes. Nothing contained herein is to be construed as an "admission" of prior art. Applicant expressly reserves the right to demonstrate, where appropriate, that the articles and methods referenced herein do not constitute prior art under the applicable statutory provisions.

In many cases of brain injury, timely detection of deleterious changes in brain health can be critical for effectively treating a primary injury or preventing a secondary injury. Although a range of neuromonitoring devices have been developed for these purposes, the most effective means of quickly and directly evaluating neuronal health is electroencephalography (EEG).

Traditional EEG utilizes a series of metallic electrodes that are affixed to a patient's scalp to record oscillatory electrical potentials naturally generated by specific cells within the brain. Although EEG has largely been used in the past for the purposes of detecting abnormal firing of neurons resulting in seizures, data has also supported the use of EEG for real-time monitoring of brain health in normal and pathological states.

For example, EEG changes are rapidly observed when cerebral blood flow drops below a critical level (cerebral ischemia). In many cases these changes can be seen prior to the development of irreversible brain damage (cerebral infarction), which allows a health care provider to perform a clinical intervention to improve brain blood flow and prevent permanent damage. Along these lines, EEG could be extremely beneficial for patients suffering from traumatic brain injury, cardiac arrest, stroke, and other acute neurological disorders in which delayed, reversible changes in brain health can occur and effective real-time monitoring of brain health would provide the opportunity for more effective and appropriate clinical intervention.

Despite major benefits that could be attributed to the use of EEG in patients with acute brain injury, practical factors have significantly limited the widespread adoption and utility of this technique for acute brain injury in the clinical setting. Such factors have concurrently limited development of approaches for automated EEG data analysis, which in the modern era is essential for continuous clinical use.

Traditional EEG is extremely technically cumbersome. To initiate recording of EEG data, a first step requires application of metal-based electrodes to the patient's scalp by a trained technician. This process is time consuming, tedious, and often needs to be repeated for patients that require prolonged monitoring and undergo various clinical interventions (as the electrodes tend to be easily dislodged due to the lack of a permanent fixative agent between electrode and skin). Effectively attaching the electrodes to the recording hardware requires numerous individual wires that are plugged into specific points on the signal amplifier (requiring specialized knowledge and experience). This requirement for a large number of individually attached wires results in challenges for streamlined care and leads to frequent disconnections and frustrations for caregivers.

An additional technical requirement for standard scalp electrode-based EEG is that a discrete "reference" electrode be used to record a baseline electrical signal against which all other recording channels are measured. This reference electrode is accompanied by a necessary second "ground" electrode which serves to provide common-mode rejection of electrical artifact generated by the hardware or electrical equipment in the local environment. Should the reference electrode, ground electrode, or both be poorly positioned or become disconnected in some fashion, the entirety of the EEG recording becomes corrupted and unusable. Thus, a trained technician must be available to constantly monitor the fidelity of an EEG recording and provide "troubleshooting" support should there be technical issues with the common reference or ground electrodes.

For these reasons, 24-hour availability of highly-trained technicians is required to effectively utilize scalp-based continuous EEG recording for brain injured patients. Unfortunately, the significant majority of clinical centers do not have the financial resources or access to trained personnel to support this process and are therefore unable to effectively offer continuous 24-hour EEG recording for brain injured patients.

Beyond the complicated technical requirements associated with long-term scalp electrode-based recording, current clinical use of EEG is largely dependent on raw electrical waveform analysis. This process requires the availability of an expert trained in the art of EEG interpretation. There are several major limitations associated with the need for such a trained expert. First, these individuals generally do not review the EEG on a continuous basis; rather, recordings are reviewed on an episodic basis which may be as infrequent as once every 24 hours. Such infrequent EEG review provides little utility for monitoring brain health in patients with neurological injuries, as relevant physiological changes are generally continuous rather than episodic. Second, concerning EEG changes that are identified in delayed fashion are often noted well after a potentially reversible secondary brain injury has become irreversible, therefore rendering delayed identification of the EEG abnormality clinically meaningless. Third, experts trained in the art of EEG interpretation are relatively rare in number and are unavailable in many settings where EEG monitoring for brain injured patients is critically important. Finally, a great deal of information that is of greatest utility for monitoring patients with brain injury cannot be see in the raw waveform data and requires quantitative analysis of EEG "power" in specific frequency bands to effectively identify changes of concern.

To this end, it is possible that physiologically useful information can readily be gained through use of mathematical processing of raw EEG signals into easily interpreted visual color displays ("Compressed Spectral Arrays" displaying EEG power in discrete frequency bands). However, requirements for a "clean" EEG signal (that which benefits from a high signal-to-noise ratio) in such analysis has terminally mitigated the clinical adoption of quantitative EEG methods using scalp-based electrodes. Current methods require human oversight to confirm the validity of processed signals and ensure that periods of contamination from artifact, noise or loss of electrode contact are not interpreted as valid EEG (which as previously noted is common with scalp EEG).

Moreover, contaminated EEG recordings can emerge from several independent sources. On the "signal" side of the equation, distance from the "generators" of the EEG signal (i.e. the neurons) and the presence of intervening tissue that dampens the signal (e.g. tissues of the scalp) serve to decrease electrical signal amplitude and increase "averaging" effects that tend to minimize overall amplitude of the EEG waveform. On the "noise" side of the equation, electromechanical factors inherent to recording with scalp electrodes are significant sources of EEG artifact. As mentioned previously, the tenuous connection between metal and skin results in the introduction of significant electrical noise and inconsistency of signal. Sources of external electrical noise are widely distributed in clinical settings in which care of brain-injured patients typically occurs (e.g. the intensive care unit) and can include a diverse array of environment-based electrical artifacts (contaminating electrical signals from other equipment, movement of the electrodes or connecting wires during clinical care activities, etc.) and patient-based artifacts (electrical signals generated by muscle activity associated with shivering, abnormalities of the skin, etc.). Critically, excessive noise, failure or loss of the common reference electrode will prohibit any useful recording from any additional electrodes spread over the cranium.

Taken together, poor signal-to-noise ratio and poor long-term fidelity of scalp-based EEG systems has precluded the development of effective automated, continuous, reliable quantitative analysis which is essential for an EEG-based neuromonitoring tool in brain injured patients. Therefore, a system is needed that allows non-expert clinical personnel to deploy electrode arrays that provide continuous high-fidelity EEG recording.

BRIEF DESCRIPTION OF THE INVENTION

This summary is provided to introduce a selection of concepts in a simplified form that are further described below in the Detailed Description. This Summary is not intended to identify key or essential features of the claimed subject matter, nor is it intended to be used to limit the scope of the claimed subject matter. Other features, details, utilities, and advantages of the claimed subject matter will be apparent from the following written Detailed Description including those aspects illustrated in the accompanying drawings and defined in the appended claims.

As described herein, one aspect of the invention is an implantable subgaleal electrode array comprising a support structure capable of being passed through the skin and implanted in the subgaleal space. The support structure of the implantable device comprises at least one reference element; at least one ground element; and one or more recording elements. This array is capable of detecting and/or transmitting a subgaleal electrical signal.

In preferred embodiments, multiple recording elements are included in the array. These multiple recording elements can be used as "back-ups" in the event that one of the recording elements becomes inactive and/or are unable to transmit accurate EEG signals. Moreover, the position of the recording elements along the support structure can vary. For example, the recording elements can be arranged linearly and/or circumferentially along the support structure. In other preferred embodiments, the reference and the ground elements can be located at the most distal contact from the array exit point.

In further preferred embodiments, the reference and/or the ground element is located just proximal to an array exit point (e.g. just below the skin). In further preferred embodiments the reference and ground elements are distributed along the array at some distance from an entry or exit point of the array. In addition, the reference and/or the ground elements can be located on contralateral arrays or collocated on the same array. In further preferred embodiments, the reference and ground elements may be present in other configurations that are distinct from the array encompassing the recording elements; for example, the reference element, ground element or both may be located upon another device designed for implantation into or on the patient. The recording elements can be distributed along the array and may be positioned proximal to, distal to, or intermingled with the reference elements, ground element, or both. In further preferred embodiments, parallel reference and ground electrodes are electrically tied together from each side at the level of the external hardware, resulting in "average" ground signal and reference signal for subsequent analysis of symmetry. Any of the above combinations are also envisioned.

The support structure of the implantable array must be made of a material capable of housing the reference, ground and recording elements. More importantly, the support structure must be capable of insertion into the subgaleal space and maintained for an extended period of time (ranging from several minutes up to several weeks). Example of preferred support structures, include but are not limited to being cylindrical in shape, made of flexible biocompatible material (such as, for example silastic or polyurethane); and/or curved in shape with a pointed tip. The diameter of the array may be as small as 0.5 mm, 0.6 mm, 0.7 mm, 0.8 mm, 0.9 mm, or 1.0 mm and as large as 1 cm, 2 cm, or 3 cm, although smaller or larger arrays are also possible. In cases where the array may be curved it would be generally intended to follow the natural curvature of the human skull and therefore would be flexible in certain cases. These structural characteristics of the support structure facilitate atraumatic passage of the array through the skin and into the subgaleal space.

As described herein, the implantable electrode array can comprise further elements to aid in the insertion, positioning and/or maintenance of the array in the subgaleal space. For example, equipment associated with the implantable electrode array may further comprise a sheath, a needle and a passage assistant attachment wherein said attachment means is capable of pushing and/or pulling the needle through the subgaleal space; an insertion guide for identifying the anatomically appropriate area for electrode entry; a retention means of the electrode at the skin entry site; a retention means of the electrode at the skin exit site; an exit guide to facilitate passage of a needle through the skin at the exit point; a needle physically associated with, connected to or otherwise part of the electrode array; and/or any combination of above.

In preferred embodiments, the electrode array is capable of being directionally tunneled in the subgaleal space in the parasagittal anterior-posterior line overlying one or both hemispheres of the brain.

In other embodiments, the implantable array is part of a system used to measure subgaleal activity. For example, the system for measuring subgaleal activity can comprise both the implantable subgaleal electrode array as described herein along with an interface connecting said implantable subgaleal electrode array to a processor. The processor can be configured to perform a number of tasks and calculations, including but not limited to:

a) detecting, filtering, processing, displaying, storing and/or transmitting brain-derived electrical signal in real time;
b) automating the selection of the reference element and/or the ground element;
c) interrogating the recording function of the reference element, the ground element and the recording element;
d) filtering and/or processing the detected electrical signals to generate uni- or multichannel electroencephalographic (EEG) data, preferentially including:
 (i) raw EEG data; or
 (ii) quantitative EEG data;
e) utilizing a range of display and recording montages including referential montages and montages derived from pairs of electrodes;
f) preassigning a recording montage to one or more recording elements;
g) continuously monitoring, identifying and excluding a reference element, ground element and/or recording element demonstrating poor signal quality, preferentially using techniques such as;
 (i) evaluation of absolute voltage;
 (ii) evaluation of voltage relative to other individual or aggregated recording elements;
 (iii) evaluation of absolute EEG power;
 (iv) evaluation of EEG power relative to other individual or aggregated recording elements;
 (v) impedance measurement of recording elements;
h) analyzing and interpreting signals between multiply implanted electrode arrays;
i) balancing montages, preferentially through selection of data from specific recording elements to provide symmetry between arrays;
j) allowing for variable or dynamic selection of specific combinations of recording elements on multiple arrays to make a up a recording or display montage;
k) performing bipolar mathematical referencing between the recording elements on an array;
l) measuring, analyzing and reporting symmetry, asymmetry or difference analysis between the two hemispheres of the brain;
m) any combination of (a)-(l).

Preassigning a recording montage to one or more recording elements can occur either by user selected combination of implanted arrays or by direct interrogation of the electrical signals/data received. Moreover, by continuously monitoring, identifying and excluding non-functional reference, ground and/or recording elements allows one to evaluate signal characteristic for each individual recording element and discard data from a specific recording element should it be deemed to be nonfunctional or artifactual.

Similarly, by using multiple implanted electrode arrays positioned bilaterally (for example), one can receive symmetrical analysis of hemispheric recordings, such that symmetry or difference analysis between the two hemispheres of the brain can be generated and evaluated. Moreover, by allowing for variable or dynamic selection of specific combinations of recording elements on multiple arrays to make a up a recording or display montage provides greater diversity of recorded intercontact electrical signal.

In preferred embodiments, the electrode array is capable of being directionally tunneled in the subgaleal space in the parasagittal anterior-posterior line overlying one or both hemispheres of the brain.

In other embodiments, the interface and the processor are integrated into each other or the array, and/or portable. Additionally, the retention element and/or the stopper are integrated with the interface and/or processor, In further preferred embodiments, the implantable electrode array and/or the system as described herein is used to measure brain activity. Brain activity can be measured in a number of in conditions, including, but not limited to brain injury, stroke, cerebral hemorrhage, intracranial hemorrhage, hypoxic/anoxic brain injury, such as, for example, as may be seen with cardiac arrest, seizure, a critical neurological injury, and/or any medical condition requiring brain monitoring.

In further preferred embodiments the system described herein can be used to detect spreading depression of the cerebral cortex.

Moreover, in further preferred embodiments, the implantable electrode array and/or the system as described herein can be used to:
a. measure brain activity during an endovascular procedure;
b. measure brain activity during a neurosurgical or vascular surgical procedure;
c. measure brain activity during a cardiac or other surgical procedure;
d assess brain injury in an acute setting, such as, for example, in an ambulance or battlefield;
e. identify laterality of brain injury or abnormality;
f. provide diagnostic information about brain health; or
g. any combination of (a)-(f).

DESCRIPTION OF THE DRAWINGS

The objects and features of the invention can be better understood with reference to the following detailed description and accompanying drawings.

FIGS. 1A and 1B depict the anatomic position of a subgaleal electrode array placed in the parasagittal plane in the midpupillary line on the right side (100), extending from the posterior/parietal insertion point (110) to the anterior/frontal exit point (120), with an extracranial extension designed for unitized insertion into a connection cable that connects to the interface/processor (130). The gray portion of the array is that which is located within the subgaleal space.

FIG. 6A is a face-on view of the exit guide (600) having a solid ring with a central opening (610) for passage of the needle.

FIG. 6B is a side cutaway view of the exit guide (600) having a taper in thickness from the outer edge (630) to the rim of the central hole (640).

FIG. 6C is a top down view of the head (650) and demonstrates a needle/sheath apparatus being placed through the subgaleal space with the exit guide (600) positioned at the proposed exit point to direct and assist exit of the needle from the subgaleal space.

FIGS. 8A and 8B are face-on and side views respectively of an exemplary posterior "stopper," 805 consisting of a small hollow cylindrical central element attached to a larger disc that will attach to the end of the array and designed to prevent pull-out of the array from the anterior exit point, which can be placed on the posterior end of the array prior to insertion (820) and secured to the skin after the final recording element on the array has passed into the subgaleal space (830).

FIGS. 8C and 8D are, face-on (840) and side (850) views respectively of an exemplary anterior "stopper," consisting of a disc with a central hole just large enough to accommodate passage of the array through the hole and designed to prevent posterior movement of an implanted array back into the subgaleal space, which can be placed over the anterior aspect of the array (860) following passage of the array through the anterior exit point (870). The retention devices can be secured using staples, sutures or alternate medically appropriate means to secure them to the skin, and once secured in place the retention devices will serve to stabilize the array within the subgaleal space as well as maintain sterility be providing coverage for the entry and exit points into the skin.

FIGS. 8F and 8G are sequential top-down views of a head with an electrode array placed in the subgaleal space and shows positioning of posterior stopper (830) and subsequently anterior stopper (870) after array insertion.

In FIG. 12A, synthetic channels are generated from bipolar comparisons of recording from adjacent channels, resulting in a total of 7 total synthetic channels. FIG. 12B represents a "skip one" approach whereby synthetic channels are generated from bipolar comparisons of every other recording element along the array. Similarly, FIG. 12C exhibits a "skip two" approach whereby synthetic channels are generated from bipolar comparisons of every third recording element along the array. The "skip" synthetic channels can thus be used to provide electrographic sampling of larger recording fields.

FIG. 14 depicts examples of the balancing function of the processor, which allows for maintenance of data symmetry between the two cerebral hemispheres in cases where an individual recording element at a specific point along a single array are identified as "bad. In this representative example, data from bilateral arrays including four recording elements each are utilized. When a particular data channel is identified as "bad" on one array (in this case, a series of "bad" channels on the right side), the processor provides concurrent exclusion of 1) the derived synthetic bipolar recording channels containing the "bad" recording element from the montage on the affected (ipsilateral/right) side, as well as 2) the matched derived synthetic bipolar channels from the unaffected (contralateral/left) side, thus maintaining symmetry of analysis and data display between the two hemispheres.

DETAILED DESCRIPTION OF THE INVENTION

Figure 2:
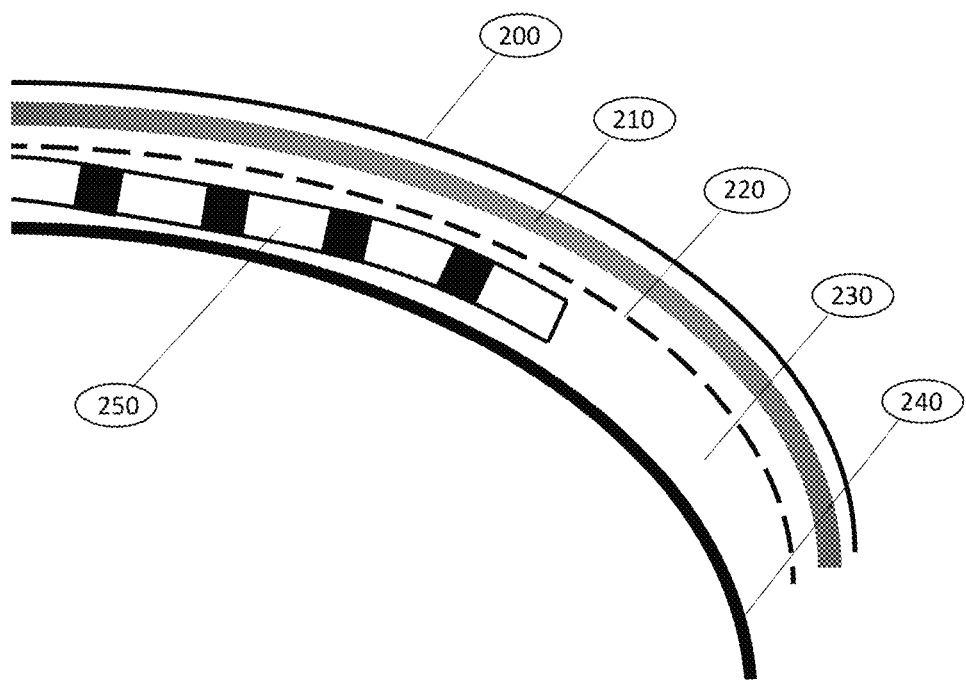
FIG. 2 is a graphical "cutaway" representation of the layers of the scalp, including epidermis (200), subcutaneous tissue (210), galea (220), subgaleal space (230), and skull (240), demonstrating an electrode array (250) within the subgaleal space between the galea and the skull after having been placed through the skin and subcutaneous tissues (200, 210, 220).

The following definitions are provided for specific terms which are used in the following written description.

Definitions

As used in the specification and claims, the singular form "a", "an" and "the" include plural references unless the context clearly dictates otherwise.

The present invention can "comprise" (open ended) or "consist essentially of" the components of the present invention. As used herein, "comprising" means the elements recited, or their equivalent in structure or function, plus any other element or elements which are not recited. The terms "having" and "including" are also to be construed as open ended unless the context suggests otherwise.

The term "about" or "approximately" means within an acceptable range for the particular value as determined by one of ordinary skill in the art, which will depend in part on how the value is measured or determined, e.g., the limitations of the measurement system. For example, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5 fold, and more preferably within 2 fold, of a value. Unless otherwise stated, the term "about" means within an acceptable error range for the particular value, such as ±1-20%, preferably ±1-10% and more preferably ±1-5%. In even further embodiments, "about" should be understood to mean+/−5%.

Where a range of values is provided, it is understood that each intervening value, between the upper and lower limit of that range and any other stated or intervening value in that stated range is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either both of those included limits are also included in the invention.

All ranges recited herein include the endpoints, including those that recite a range "between" two values. Terms such as "about," "generally," "substantially," "approximately" and the like are to be construed as modifying a term or value such that it is not an absolute, but does not read on the prior art. Such terms will be defined by the circumstances and the terms that they modify as those terms are understood by one of skill in the art. This includes, at very least, the degree of expected experimental error, technique error and instrument error for a given technique used to measure a value.

Where used herein, the term "and/or" when used in a list of two or more items means that any one of the listed characteristics can be present, or any combination of two or more of the listed characteristics can be present. For example, if a composition is described as containing characteristics A, B, and/or C, the composition can contain A feature alone; B alone; C alone; A and B in combination; A and C in combination; B and C in combination; or A, B, and C in combination.

As used herein, the term "determining" encompasses a wide variety of actions. For example, "determining" may include calculating, computing, processing, deriving, investigating, looking up (e.g. looking up in a table, a database or another data structure), ascertaining and the like. Also, "determining" may include receiving (e.g. receiving information), accessing (e.g. accessing data in a memory) and the like. Also, "determining" may include resolving, selecting, choosing, establishing and the like.

As used herein, "implantable subgaleal electrode array", "implantable electrode array", and "implantable array" are used interchangeably. The implantable electrode array is designed to pass through the skin and be implanted into the subgaleal space. The implantable electrode array comprises one or more recording element(s), a reference element, and a ground element. These elements may be constructed of metal, plastic, or other compounds.

As used herein, a "reference element" refers to a contact (preferably also made of metal) designed to act as a common member of variable electrode pairs as a control allowing for the comparison of subgaleal brain activity detected by one or more recording elements on the implantable array. For example, the reference sensor can allow for comparison of subgaleal brain activity detected by multiple recording elements.

As used herein, a "ground element" refers a recording element which serves to provide information about globally recorded electrical signals that derive from non-physiological sources (such as local electrical equipment) and therefore allow for common-mode rejection of such non-physiological signals.

As used herein, a "recording element" is a contact which is capable of detecting subgaleal brain electrical activity. Preferably, the recording element is metallic.

As used herein, the "subgaleal space" refers to the anatomic compartment of the scalp which lies below the epidermis and galea aponeurosis (the fascial layer of the scalp) and the periosteum and bone of the skull. The subgaleal space is a naturally occurring, avascular region that can be easily accessed and traversed using specialized tools without risk of significant injury, bleeding, risk of intracranial infection, or other major medical complication.

As used herein, the "support structure" refers to a structure (a) capable of housing the reference, the ground and the recording elements; (b) capable of transmitting the electrical signal generated by the brain to the associated processor; and (c) capable being inserted through the skin and maintained in the subgaleal space. The support structure may be designed for passage through a separate piece of equipment that is tunneled through the subgaleal space, or the support structure itself may contain the necessary elements to allow for independent passage.

As used herein "circumferential arrangement" is defined as fully wrapping around the support structure so that geographically specific electrical signals (for example those originating only on one side of the array) can be recorded no matter the rotational position of the array in relation to the electrical signal. This therefore allows for pandirectional recordings with optimal tissue contact and/or eliminates need for a specific orientation of the device within the subgaleal space.

As used herein "directional tunneling" refers to passage of an array from a specific entry point in an anatomically relevant manner to allow recording of brain signals of interest. For example, an array that is directionally tunneled from the back of the head to the front of the head (i.e. the parasagittal plane) will allow for recording of the frontal and parietal lobes, while an array that is directionally tunneled from the medial aspect of the head to the lateral aspect of the head (i.e. the coronal plane) will allow of recording from a single lobe (e.g. frontal lobe, parietal lobe) in isolation depending on the anterior/posterior position of the trajectory.

As used herein, the "array exit point" refers to the point on the scalp where an electrode array leaves the subgaleal space, traverses the overlying tissues and exits the scalp to the outside environment.

As used herein, "contralateral arrays" refer to arrays that are implanted on the opposite side of the head from the array of interest (which by convention is termed the ipsilateral array).

As used herein, a "sheath" refers to a hollow structure of a diameter designed to accommodate an electrode array that allows for passage of the array through the subgaleal space in a manner that is minimally traumatic to the surrounding tissues and the array itself. The sheath may be made out of a flexible plastic (e.g. silastic or polyurethane), metal or another material and may either be disposable or re-usable. The sheath may be cylindrical to allow for atraumatic passage through the tissues of the scalp but may adopt other conformations to accommodate alternate array designs.

As used herein, a "needle" refers to a piece of hardware with a sharp aspect designed to penetrate the scalp in minimally traumatic fashion. The tip may be tapered to a point to minimize the "cutting" or laceration of the scalp and minimize the resulting size of an entry or exit point from the scalp. The needle may be cylindrical to minimize injury to the tissues of the scalp but may also adopt other specific confirmations related to the design of a particular array or associated sheath. The diameter may range from as small as 0.5 mm, 0.6 mm, 0.7 mm, 0.8 mm, 0.9 mm, or 1.0 millimeter to up to 1 cm, 2 cm, or 3 centimeters. The needle may be metal or plastic in origin and has material characteristics that are stiff enough to allow for directional tunneling but may be flexible enough so that shaping of the needle prior to or during insertion allows for optimal passage with the natural curvature of an individual skull. The needle may include modifications that assist with passage through the tissue of the scalp, for example a removable attachment that can augment a clinician's ability to "push" or "pull" the needle through the tissue of the scalp.

As used herein, an "insertion guide" refers to a structure capable of identifying the anatomically appropriate area for electrode entry. For example, an array that is intended to be inserted in the parasagittal plane overlying the watershed zone between the major vascular territories of the frontal and parietal lobes would be best placed in a line that is externally continuous with the pupil or lateral canthus of the eye. The insertion guide in this case would allow the user to identify the proposed linear position of entry and exit points along this line on the scalp. In addition, the insertion guide may provide reference points to the clinician regarding the optimal insertion and electrode points for an array based on the natural points of curvature of the human skull, notably at the mid-parietal and mid-frontal regions.

As used herein, a "retention means", "retention device" or "retention element" refers to a structure that either permanently or temporarily affixed to the implantable electrode array, that can be secured to the skin or otherwise positioned to prevent the array from being dislodged or pulled through at the exit site from the skin. With some embodiments of the invention, the retention means may be easily removed to facilitate bedside removal of the array. Such retention means can be positioned either at the skin entry site or exit site (or both) and ensures appropriate placement and positioning of the implantable device. Examples of such retention means, include but are not limited to 1) plastic "stoppers" that attach to the end of an array that may cover an entry site, attach to the skin and firmly secure the array from further forward movement, or 2) plastic discs that may be placed over the array that limit array movement by friction and can be secured to the scalp to prevent backwards movement of the array into the subgaleal space. In addition, the retention means can serve to cover the insertion and exit points and provide for greater sterility of the array within the subcutaneous tissues. The retention means may either be permanently affixed to the array (e.g. physically part of the support structure) or separately applied to the array during or after an insertion procedure. The retention means may also be integrated with the interface and/or processor, such that the interface and/or the processor are included as part of the retention means.

As used herein, an "exit guide" refers to a structure that serves to "catch" the needle and/or sheath to optimize exit of the array from the preferred exit point from the subgaleal space to the external environment. The exit guide can allow the clinician to target a specific exit point on the scalp and provide a physical means by which the needle and/or sheath are physically targeted to the intended exit point. This can be accomplished through a combination of pressure from the exit guide on the scalp surrounding the proposed exit point with a central area in the exit guide which encompasses the proposed exit point where there is no pressure on the underlying scalp. The exit guide may be circular in shape with a central hollow region through which passage of the needle, sheath and/or array occurs. The exit guide may be circumferentially tapered towards the central hollow region to assist in needle passage through the skin.

As used herein, a "montage" refers to a specific manner in which recorded electrical signals are displayed. A montage may be predetermined by the processor or may be user-defined. The montage can be altered to include recordings from particular electrode pairs of interest and may display electrical signals as initially recorded ("referential channels") or signals that are generated through secondary mathematic combinations of referential recordings ("synthetic channels"). In this manner, a "recording montage" or a "referential montage" refers to signals derived in primary fashion based on the specific relative locations of the recording elements to the reference electrode and the relative position of an individual recording element along an array, while a "bipolar montage" is a display utilizing mathematical comparisons of referential recordings from separate recording elements of interest along one or more arrays.

As used herein, a "processor" is capable of modifying, analyzing, correlating, storing and displaying recorded subgaleal brain electrical activity. The processor may comprise hardware and/or software elements.

As used herein, "subgaleal brain activity" is defined as the electrical signals generated by the brain that are recorded from within the subgaleal compartment of the brain. As described herein, "subgaleal brain activity" or "subgaleal brain electrical activity" can be measured by a variety of different parameters capable of detecting and/or measuring electrical activity, including, but not limited to: (a) average voltage level; (b) root mean square (rms) voltage level and/or a peak voltage level; (c) derivatives involving fast Fourier transform (FFT) of recorded brain activity, possibly including spectrogram, spectral edge, peak values, phase spectrogram, power, or power ratio; also including variations of calculated power such as average power level, rms power level and/or a peak power level; (d) measures derived from spectral analysis such as power spectrum analysis; bispectrum analysis; density; coherence; signal correlation and convolution; (e) measures derived from signal modeling such as linear predictive modeling or autogressive modeling; (f) integrated amplitude; (g) peak envelope or amplitude peak envelope; (h) periodic evolution; (i) suppression ratio; (j) coherence of calculated values such as spectrogram, spectral edge, peak values, phase spectrogram, power, and/or power ratio; (k) wavelet transform of recorded electrical signals, including spectrogram, spectral edge, peak values, phase spectrogram, power, or power ratio of measured brain activity; (l) wavelet atoms; (m) bispectrum, autocorrelation, cross bispectrum or cross correlation analysis; or (n) waveform phase reversal, or other alteration of waveform characteristics related to dipole, resulting in variable positive or negative values between recording elements and reference sensors at specific moments in time. In preferred embodiments, the subgaleal brain activity is measured by categorical measurements, such as, for example, from volts (V), hertz (Hz), and/or or derivatives and/or ratios thereof.

As used herein, the system can provide information regarding subgaleal brain activity in a "continuous" and/or in a "real-time" fashion, allowing for optimized detection of brain activity.

As used herein, the implantable subgaleal array is designed for temporary (i.e., minutes to hours), acute (i.e., hours to days), or semi-chronic (i.e., days to weeks) implantation in a patient.

As used herein the recording element may be positioned "in proximity with" other elements on the implantable array. "In proximity with" is defined as "at, within or associated with" the specified element.

It will be further understood that when an element is referred to as being "on", "attached", "connected" or "coupled" to another element, it can be directly on or above, or connected or coupled to, the other element or intervening elements can be present. In contrast, when an element is referred to as being "directly on", "directly attached", "directly connected" or "directly coupled" to another element, there are no intervening elements present. Other words used to describe the relationship between elements should be interpreted in a like fashion (e.g., "between" versus "directly between," "adjacent" versus "directly adjacent," etc.).

Spatially relative terms, such as "beneath," "below," "lower," "above," "upper" and the like may be used to describe an element and/or feature's relationship to another element(s) and/or feature(s) as, for example, illustrated in the figures. It will be understood that the spatially relative terms are intended to encompass different orientations of the system in use and/or operation in addition to the orientation depicted in the figures. For example, if the system in a figure is turned over, elements described as "below" and/or "beneath" other elements or features would then be oriented "above" the other elements or features. The system can be otherwise oriented (e.g., rotated 90 degrees or at other orientations) and the spatially relative descriptors used herein interpreted accordingly.

Implantable Subgaleal Electrode Array

We have developed systems and methods by which an implantable subgaleal electrode array can be inserted at the bedside into the subgaleal space of a patient by clinical personnel to provide continuous high-fidelity EEG recording. Examples have been provided in the Figures as described above.

In further examples (not shown), the reference element and/or the ground element may be in the form of a wire extending longitudinally along the array.

Figure 15:
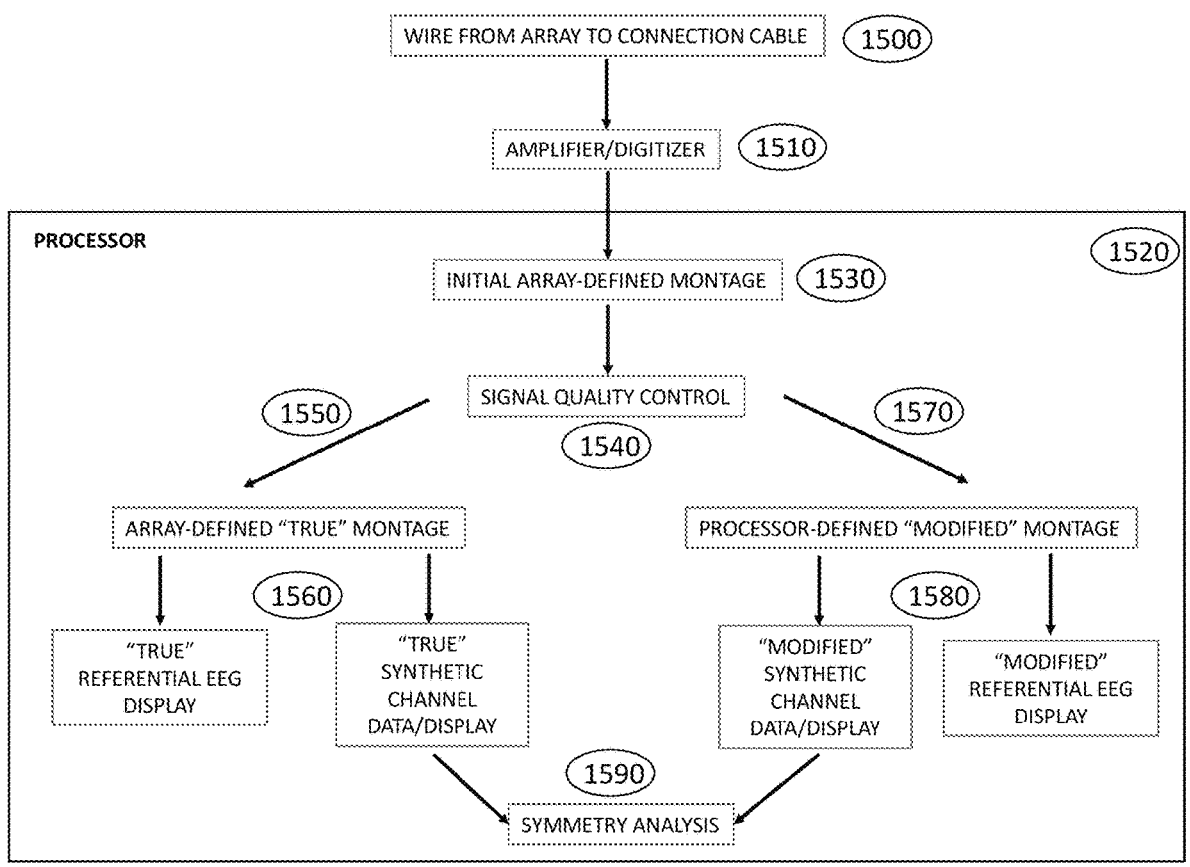
FIG. 15 provides a basic overview of signal processing and display associated with the system. Raw electrical signals are transmitted through a connection cable (1500) to an interface element (1510) which contains signal amplifiers, basic filters and analog-to-digital processing functions. The digitized signal is then transmitted to the processor element (1520) which performs an initial function to organize and interpret signal data through specific montages predetermined for particular array configurations as identified by the clinician user for an individual patient (1530). Data channels thus identified are continuously interrogated by a signal analysis function (1540) which utilizes a range of quality control measures to identify "good" and "bad" (if any) recording elements. In cases where no bad recording elements are identified, the processor provides the "true" data for review and quantitative analysis (1550) with display of "true" referential EEG signals and "true" synthetic bipolar channels derived from the input channels (1560). In cases where the quality control element (1540) identifies a "bad" contact (1560), associated referential EEG signals and the associated synthetic channels are modified by the processor to exclude data derived from the "bad" contact along with the matched channels on the contralateral array (1570) to provide "modified" referential EEG data and "modified" synthetic bipolar channels (1580). Data from either the "true" analysis or the "modified" analysis are thus available for subsequent valid symmetry analysis between the two hemispheres (1590).

The array, such as array (250) shown in FIG. 2, is specifically configured and positioned to gather hemispheric EEG data, a capability that is of relevance for patients with brain injury. An associated external processor element, such as the processor element (1520) shown in FIG. 15, can be configured to record aspects of the array, including preassignment of the ground and reference electrodes. Such configurations can minimize the need for technical expertise in initiating and maintaining the recording derived from the array and, in some circumstances, can limit the number of wires that are associated with the patient. In preferred embodiments, the system automatically monitors the fidelity of signal from individual recording elements to ensure that the recorded electrical activity is valid. In cases where bilateral arrays are deployed the system will "balance" the recording montage should there be specific non-functional recording elements on one side or the other that may influence evaluation of EEG symmetry between the two cerebral hemispheres.

The approach of placing the array in the subgaleal space takes advantage of specific characteristics of this anatomic location for temporary targeting of devices in the clinical setting by personnel with no specialized surgical training or prior experience with electrode implantation. There are no major blood vessels or other sensitive tissues in this region that could be injured and result in clinical complication. In preferred embodiments, the method requires no incision as the array can be implanted into the subgaleal space using a needle and therefore, limits the risk of infection associated with device placement. In this embodiment, as the insertion technique requires only a needle for placing the arrays there is no need for a patient to be taken to the operating room for device insertion, allowing the procedure to be performed at the bedside in the intensive care unit, in the emergency room, in an ambulance en route the hospital, or in a patient's home etc. In other preferred embodiments, the use of the needle along with an associated sheath to pass the electrode through the skin minimizes trauma to the traversed tissues and minimizes the chance of subgaleal "pocket" formation as may occur with the use of a larger trocar (thereby leading to potential poor contact of the electrode array with the surrounding tissues).

Other benefits of the use of the implantable subgaleal electrode array as described herein include a low risk of developing systemic infection should there be a local infection with an implanted array, as there is no involvement of a major fluid compartment (such as the cerebrospinal fluid) or intravascular space. In cases where a local infection is suspected, the method of insertion and stabilization allows for easy bedside removal the devices without the need for a formal surgical procedure. The presence of the underlying skull prevents any possibility of brain injury during insertion. The natural plane of separation between the galea and the underlying skull makes passage of a device very easy in this plane, therefore requiring no specialized anatomic knowledge or surgical training.

Moreover, insertion of the implantable electrode array into the subgaleal space takes advantage of conserved similarities in human cranial and brain anatomy, notably the position of the largest lobes of the brain (frontal and parietal), the specifics of cranial proportions and commonalities of the major regions of blood supply. Positioning the implantable array as described herein provides coverage over the lateral bulk of the frontal and parietal lobes which is typically the "watershed" zone between major blood vessels supplying the majority of the brain (anterior cerebral artery and middle cerebral artery). This is the region that is at greatest metabolic risk in cases of decreased blood flow due to inherent limitations of flow and is therefore of greatest interest for EEG monitoring.

Means for Implantation and Maintenance of the Implantable Arrays

As described herein, implantable electrode arrays are designed for insertion at the bedside by clinical personnel without specialized surgical expertise. Moreover, in preferred embodiments, the described arrays are designed for temporary use (e.g., for example minutes to weeks), can be easily removed at the bedside (for example in cases where subgaleal EEG is recording is no longer clinical indicated), and can be inserted using only local anesthetic with minimal risk to the patient, as placement is outside the skull, no major anatomic structures are at threat, and the array is not placed within access to the blood stream or other fluid compartments with physiological extension to the body or brain.

Figure 7A:
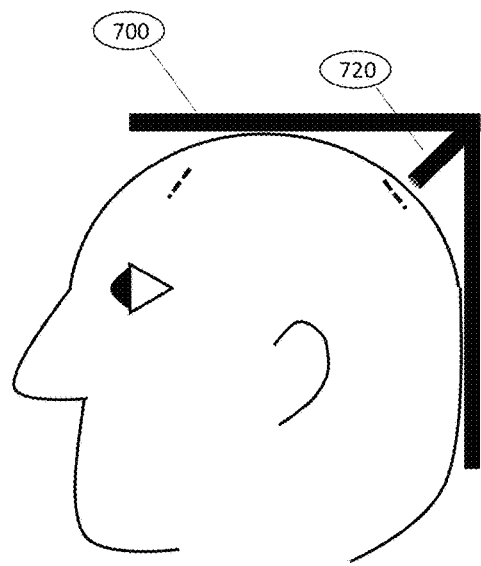
FIGS. 7A and 7B provide lateral and top-down views respectively of a needle insertion guide (700), designed to identify the appropriate trajectory in the midpupillary line (710) and an entry point at the parietal curvature of the skull (720).
Figure 7B:
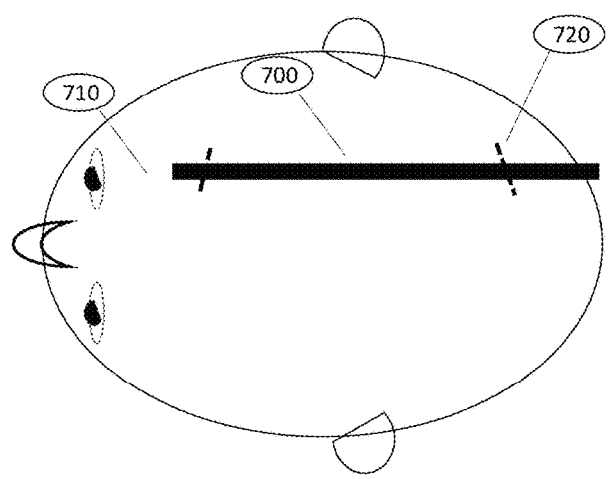
Figure 8A:
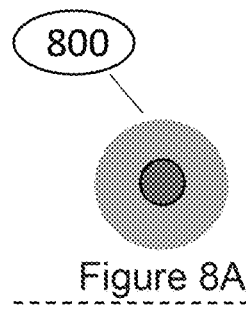
FIGS. 8A to 8G depict array retention devices to assist with securing an array that has been placed into the subgaleal space.
Figure 8B:
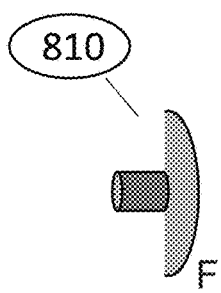
Figure 8C:
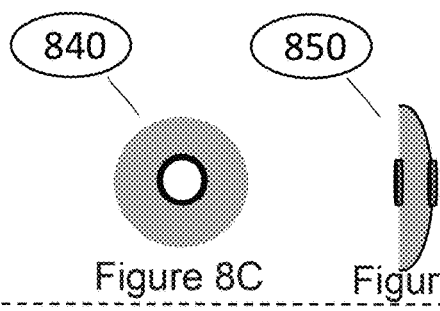
Figure 8D:
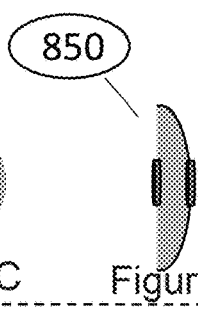
Figure 8E:
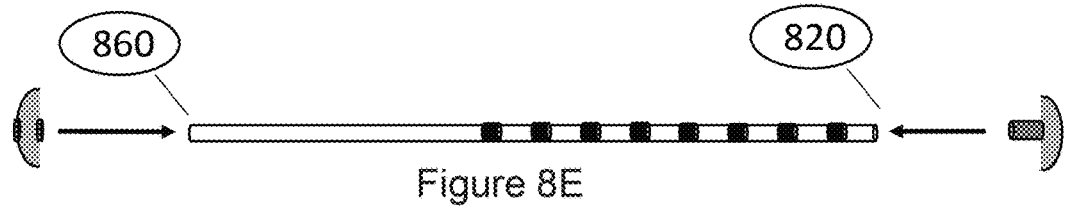
Figure 8F:
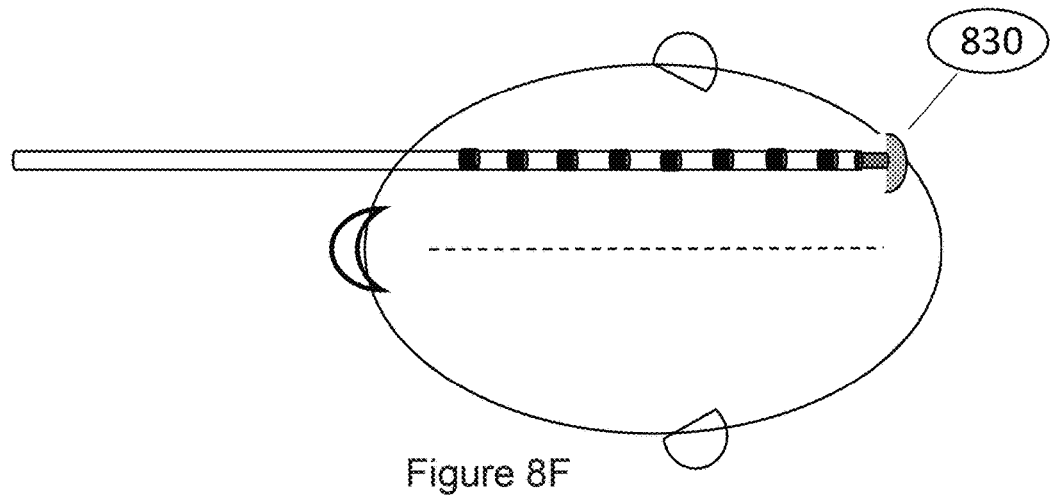
Figure 8G:
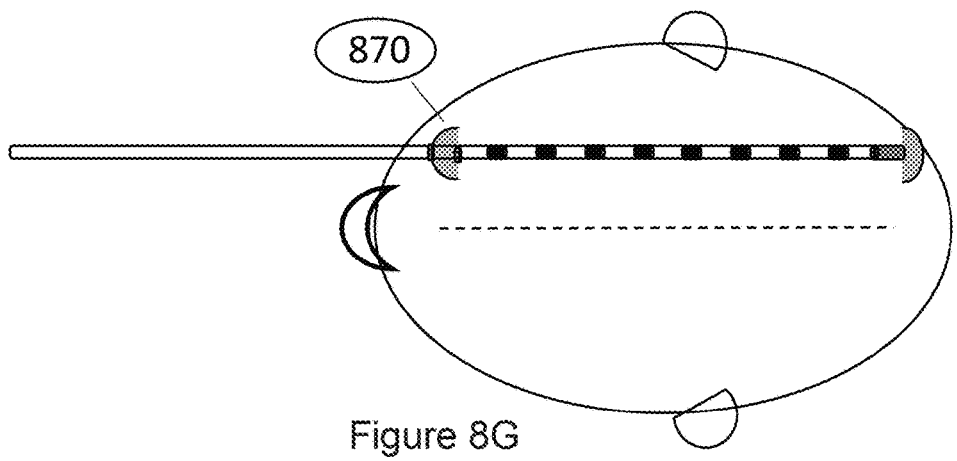
Figure 9:
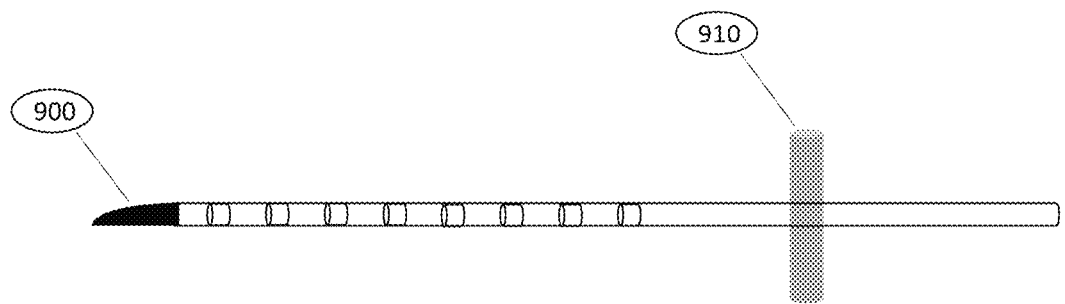
FIG. 9 depicts a unitized assembly by which the insertion needle is a part of the electrode array (900) and includes a retention element distal to the last recording element designed to secure the array at the point of entry into the scalp (910).
Figures 10A, 10B:
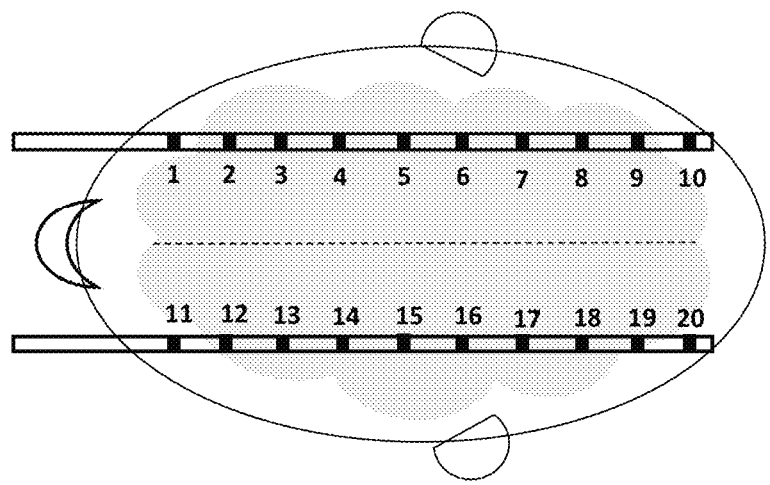
FIGS. 10A and 10B provide a representative example of numerical channel assignments for bilateral subgaleal electrode arrays including ground (numbers 10 and 20), reference (numbers 9 and 19), and individual recording elements (remaining contacts).
Figures 11A, 11B:
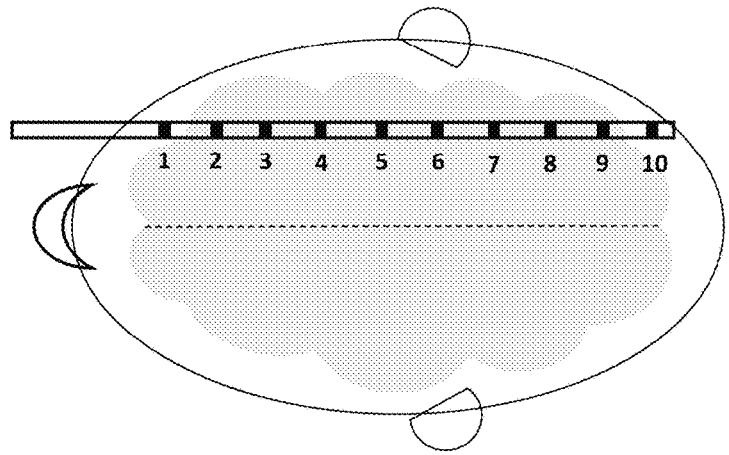
FIGS. 11A and 11B provide a representative example of channel assignments for a unilateral subgaleal electrode array including ground, reference and individual recording elements, in this case using an alternate arrangement of reference (number 5) and ground (number 10) positioning in relationship to the remainder of recording elements on the array.
Figure 12A:
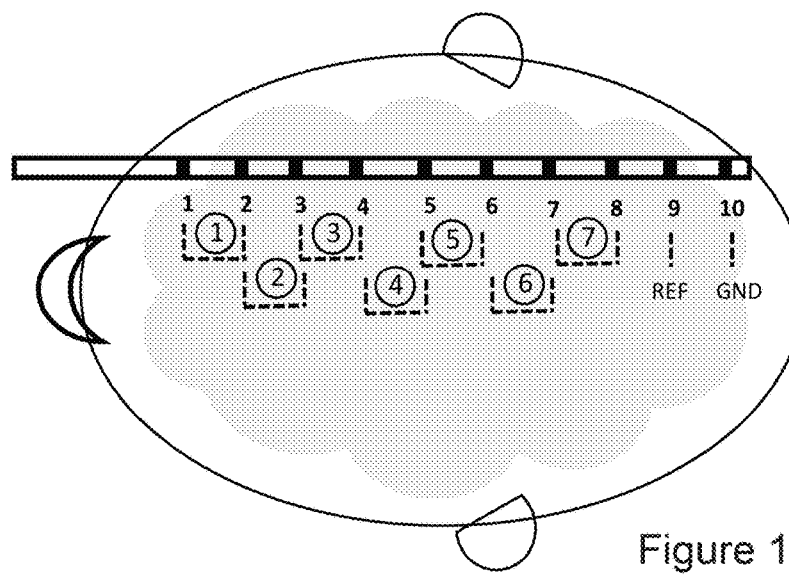
FIGS. 12A, 12B and 12C depict strategies for selecting recording channel pairs to generate synthetic channels in a bipolar recording montage.
Figure 12B:
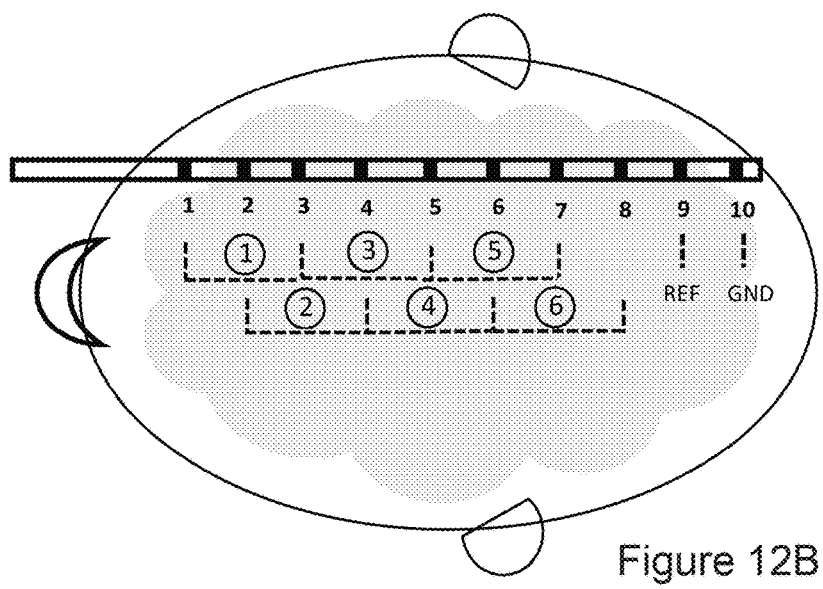
Figure 12C:
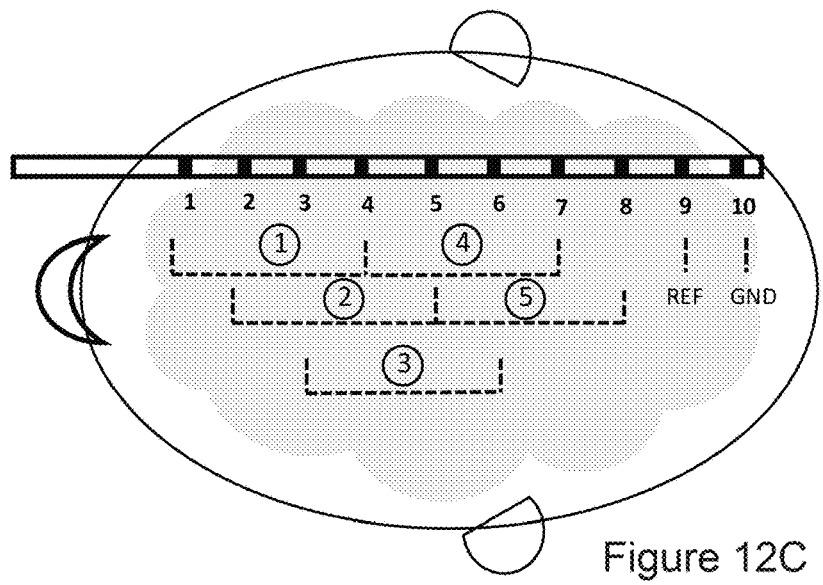
Figure 13:
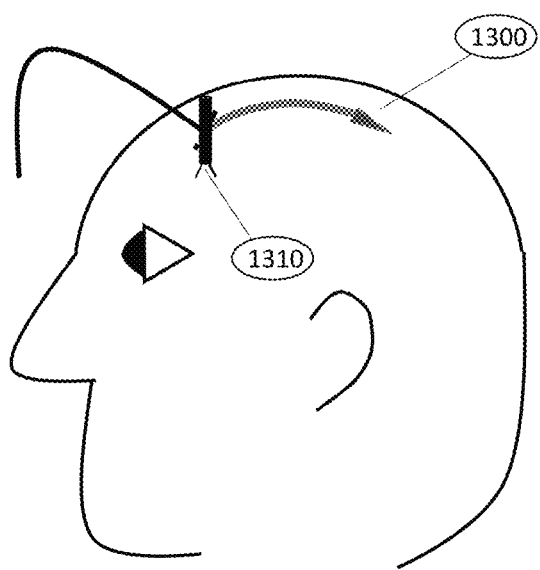
FIG. 13 provides a lateral view of a subgaleal array with integrated needle and stopper device (1300) which is inserted and secured at a single entry point (1310) in the frontal region without need for a secondary exit point. The gray portion of the array indicates that which is located within the subgaleal space.

In preferred embodiments, the implantable array is designed to be passed in a linear parasagittal plane in an anterior-posterior orientation in the ipsilateral pupillary line to allow for anatomically relevant hemispheric monitoring. In such cases the "insertion" guide would assist the clinician in identifying the appropriate entry and exit points for the array prior to passage of the array through the subgaleal space and optimize subsequent electrode positioning in the parasagittal line of interest. In some cases the insertion guide could be an L-shaped tool with a 90-degree elbow designed to be physically placed on the skull in line with the pupillary line, which will allow the clinician to 1) confirm the planned trajectory of the implanted array, 2) mark the entry point at the parietal or frontal curvature of the skull (which would be identified on the scalp as the point representing the 45 degree angle from the elbow of the insertion guide), and 3) mark the proposed exit point at the frontal aspect of the scalp which would allow for the entirety of the length of the implanted array to reside within the subgaleal space (based on the known length of the array itself). An example of such a tool in the form of a needle insertion guide (750), are shown FIGS. 7A and 7B.

Figure 3A:
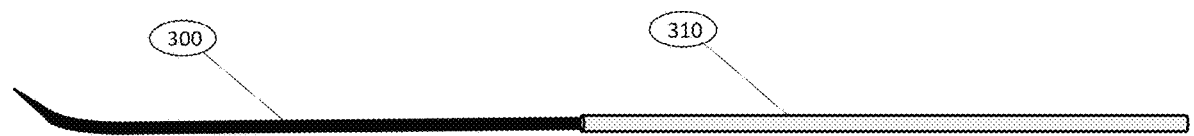
FIGS. 3A, 3B and 3C depict needle devices, each with attached sheath (310), designed for atraumatic passage of an electrode array into the subgaleal space. Three different needle examples are shown in FIGS. 3A, 3B and 3C, 300, 320 and 330 respectively. The needle tip may be straight (320) or angled (330) to facilitate passage through the subgaleal space as is illustrated in FIGS. 3B and 3C. The needle itself may be curved to conform to the natural curvature of the skull as is indicated by needle portion (340) shown in FIG. 3C.
Figure 3B:
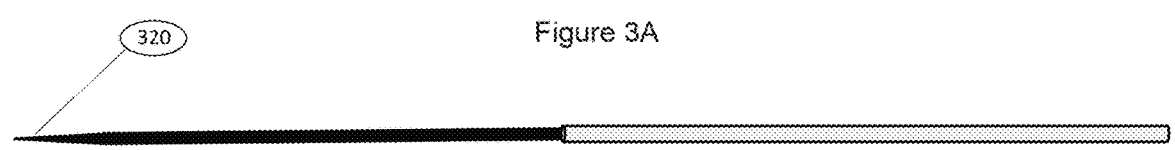
Figure 3C:
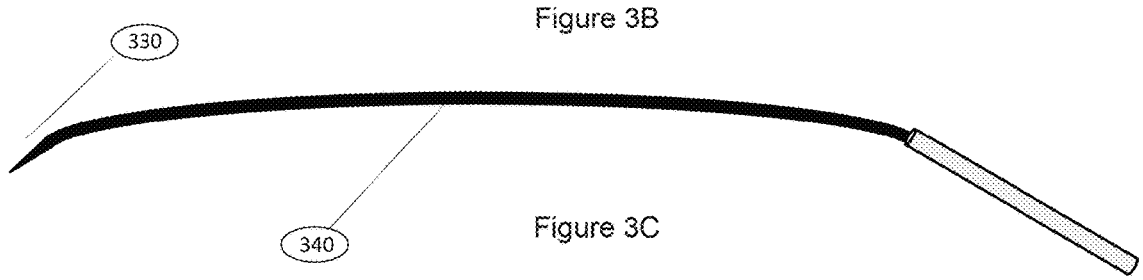
Figures 4A, 4B, 4C:
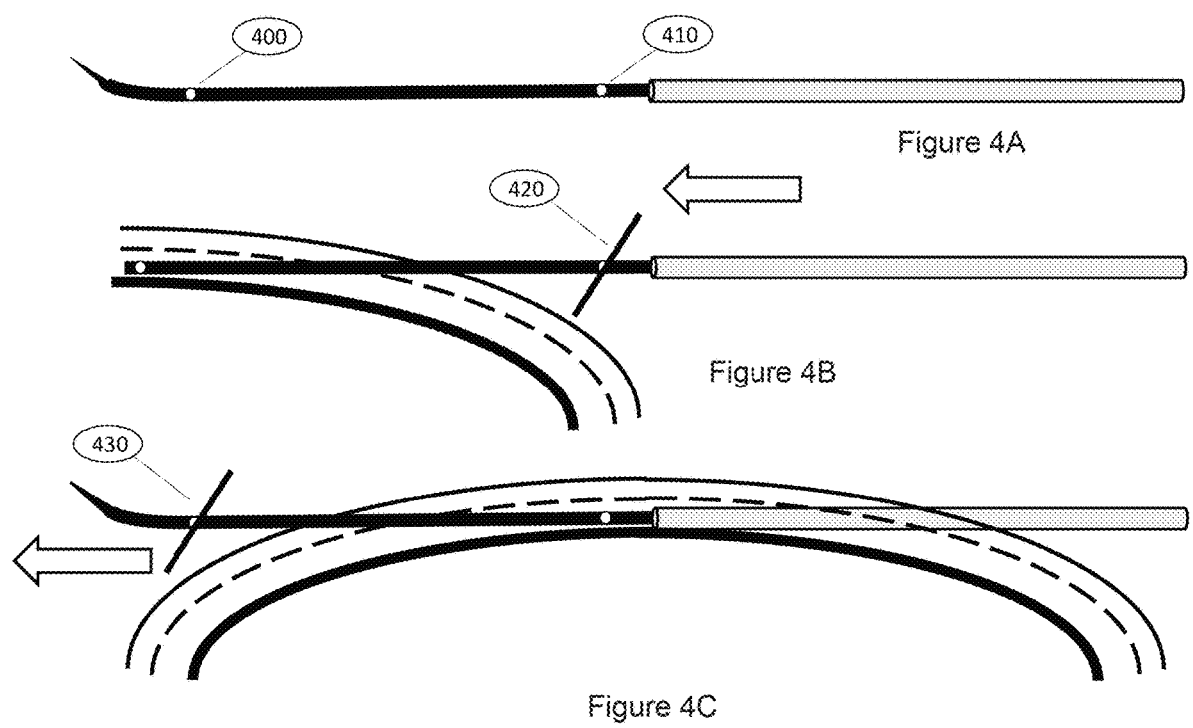
FIGS. 4A, 4B and 4C illustrate the points of attachment and means of use for the needle passage assistant in relation to the needle and sheath apparatus for subgaleal array positioning; holes are present at the front (400) and back (410) of the needle through which the passage assistant can be placed for "push" (420) and "pull" (430) assistance.
Figure 5:
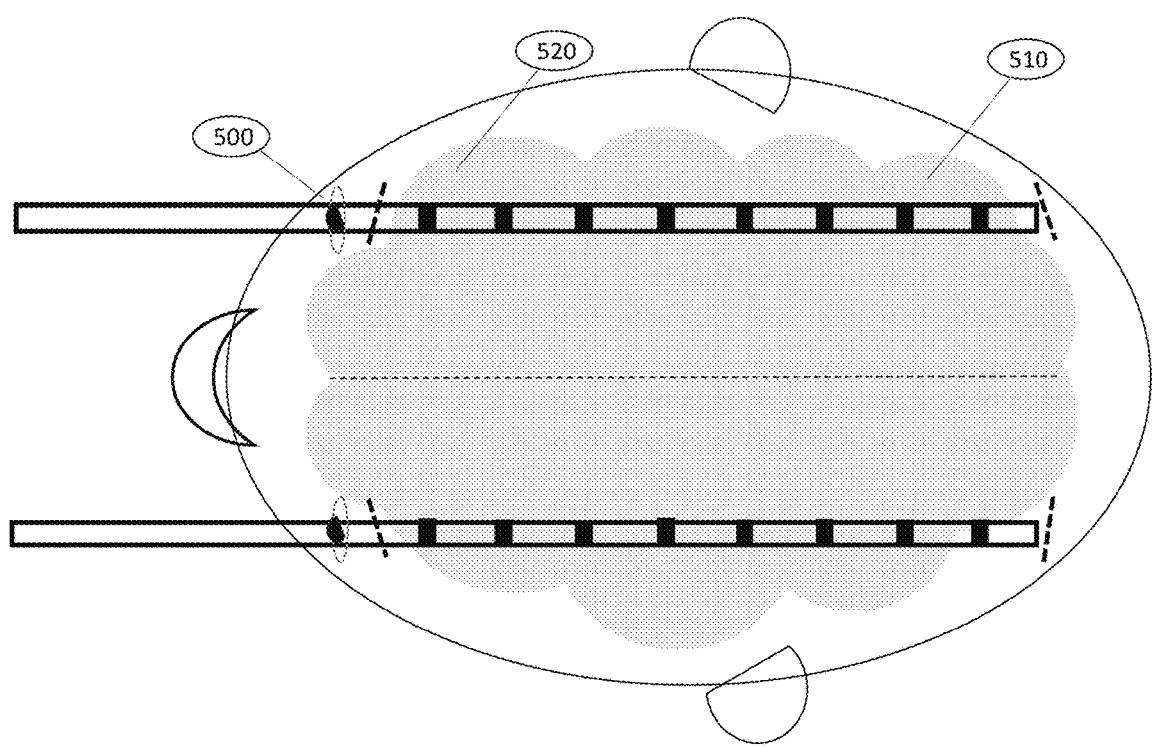
FIG. 5 provides a top-down view of a head with symmetric bilateral electrode arrays placed in the subgaleal space in the parasagittal midpupillary line (500) overlying the parietal (510) and frontal (520) regions.

In other preferred embodiments, the system includes additional hardware used to streamline and simplify insertion technique. For example, the system could comprise a needle to pass the implantable array into the subgaleal space such as the needles 300, 320 and 330 shown in FIGS. 3A, 3B and 3C. In such embodiments, the needle could have a tapered tip to minimize injury to skin and subcutaneous tissues. The needle could also have a curve at the end to facilitate passage into and out of the subgaleal space, and there may be a hollow sheath attached to the needle through which the array is passed to be deployed in the subgaleal space. In some embodiments, the needle may be inserted at one point and exit at a second point or it may be hollow and only enter for deposition of the array within the subgaleal space. Additionally, the array may include temporary plastic "stoppers" to be placed at entry and/or exit points to secure the implantable array to the skin. Such stoppers may also include the interface and/or the processor. In some embodiments, the needle may have a removable cross-piece that assists with push and pull aspects of the insertion procedure.

In some cases, such as where a shorter array is of potential use, it may be deployed using a hollow needle where there is a single point of insertion without a secondary exit through the skin; in this case the needle would be passed into the subgaleal space and the implantable electrode array is inserted through the needle, with the needle subsequently withdrawn over the electrode array and a stopper then applied to secure the electrode in place.

Figure 6A:
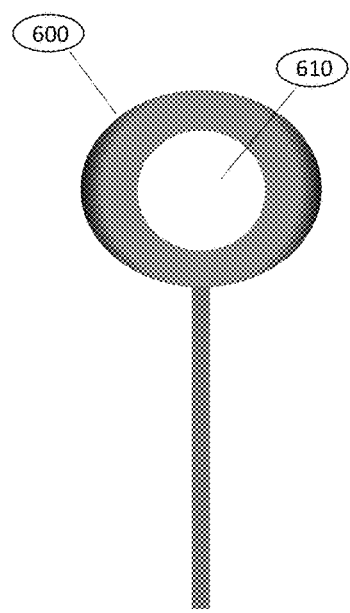
FIGS. 6A, 6B and 6C demonstrate characteristics and means of use for a needle exit guide (600) designed to assist with needle passage through a proposed point of egress from the subgaleal space.
Figure 6B:
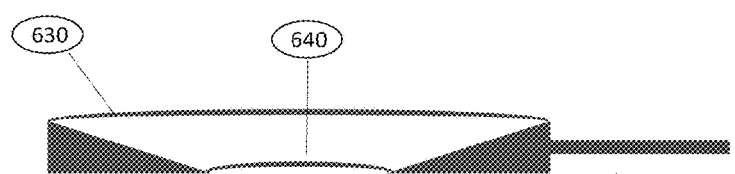
Figure 6C:
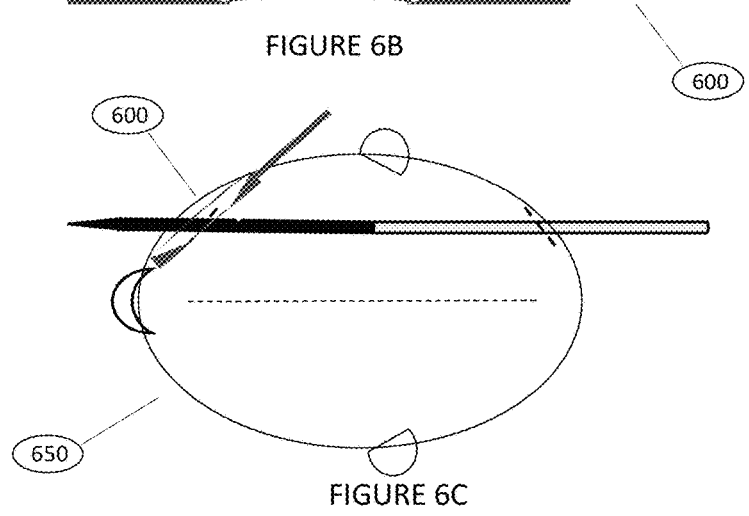

Other preferred embodiments include an "exit guide" that assists the clinician with localizing and optimizing passage of the needle, sheath and/or array from the desired exit point through the scalp. An example of such an exit guide 600 is provided in FIG. 6A.

Associated Hardware

In preferred embodiments, external hardware to which a single lead from each implantable electrode array can be connected to amplify/digitize/filter recorded EEG signals As described herein, the connected processor is capable of recording, analyzing, and displaying raw EEG signals from arrays In preferred embodiments, the processor includes predetermined "templates" that the user can select depending on the specific nature of the arrays implanted in a particular patient (unilateral, bilateral, etc.) and are critical for identifying the appropriate reference, ground and recording elements. For example, in cases where bilateral subgaleal arrays are deployed and appropriate template is selected by the user, the ground element may be identified by the processor as the most distal contact from the array exit point on one array while the reference is the most distal contact on the other array. In another representative example where a unilateral subgaleal array may be deployed, the template may identify the ground element as the most distal contact from the array exit point and the reference element as the most proximal contact from the array exit point. In other embodiments, templates may be available that are specific for arrays encompassing different numbers of recording elements with divergent spacing between recording elements. The existence of these templates thus allows the user to avoid the need to input specifics of the ground element, reference element, or recording elements on a patient-by-patient or array-to-array basis. More specifically, this allows the user to have no specialized knowledge or technical skill with the art of EEG to provide durable and effective functional EEG recording from subgaleal arrays.

In further preferred embodiments, the processor includes a real-time analytical function which interrogates qualities of electrical signals from individual recording elements on the array to confirm the veracity of recording, and if poor signals are recorded (i.e. extremely low amplitude indicating lack of contact with tissue or an incorrectly connected array, or extremely high amplitude indicating electrical artifact generated by non-physiological sources) the processor identifies that contact as a "bad channel." The user can thus be warned to pursue simple interventions to ensure that an array of interest is appropriately connected. In other cases, the processor would automatically switch use of recording elements to those providing electrophysiologically appropriate signals. Through this continuous monitoring and potential switching activity the processor thereby 1) providing an immediate and automated method to confirm high-fidelity reference and ground channels which are essential for effective EEG recording; 2) allows the user to have no specialized knowledge or experience with the technical aspects of EEG recording; and 3) automatically maintains maximum fidelity of EEG recording throughout a recording period without need to replace or monitor the fidelity of the reference or ground lead or specific recording elements along an array.

In some cases the processor may display and store EEG data in a bipolar referential montage, whereby adjacent contacts are mathematically compared to provide bipolar referencing for analysis. In some cases bipolar referential comparisons may use a "skip one," "skip two" or "skip more" approach to provide greater geographic coverage of the underlying brain. Such bipolar comparisons are generated through mathematical combination of the referential recordings from specific recording elements (i.e. the common reference recordings) to derive a synthetic electrical signal that is representative of the difference in electrical activity in the geographic region of the brain subtended by the two recording elements included in the bipolar comparison.

In additional embodiments, the processor will include analytical functions that perform automated quantitative analysis on recorded EEG signals; such analysis may include derivatives involving fast Fourier transform (FFT) of recorded brain activity, possibly including spectrogram, spectral edge, peak values, phase spectrogram, power, or power ratio; also including variations of calculated power such as average power level, rms power level and/or a peak power level; measures derived from spectral analysis such as power spectrum analysis; bispectrum analysis; density; coherence; signal correlation and convolution; measures derived from signal modeling such as linear predictive modeling or autogressive modeling; integrated amplitude; peak envelope or amplitude peak envelope; periodic evolution; suppression ratio; coherence and phase delays; wave let transform of recorded electrical signals, including spectrogram, spectral edge, peak values, phase spectrogram, power, or power ratio of measured brain activity; wavelet atoms; bispectrum, autocorrelation, cross bispectrum or cross correlation analysis; data derived from a neural network, a recursive neural network or deep learning techniques; or identification of a region of an array detecting local minimum or maximum of parameters derived from any of the above In cases of bilateral monitoring, the processor will also include a "balancing" function that includes and displays equivalent channels from each array in order to provide symmetrical data for each hemisphere of the brain. Maintaining symmetry of data acquisition and display can be critical when a clinician desires to compare aggregate electrical activity on the two sides of the brain in order to identify possible asymmetry of electrical activity. For example, in cases where injury or neurophysiological aberration may affect one side of the brain ("unilateral abnormality"), there may be diminished or otherwise altered brain electrical activity in the affected hemisphere in comparison to the contralateral ("unaffected") hemisphere. In contrast, in cases where both hemispheres are affected in equivalent fashion by injury or physiological aberration ("bilateral abnormality") it would be expected that signals from both hemispheres would be symmetrically decreased. However, such analysis requires that the nature of source data is equivalent between the two hemispheres (e.g. is data recorded from the same anatomic locations and electrographic "fields"); any asymmetry of electrode location or distance can lead to spurious comparisons. In cases where a particular recording element on one array may be excluded by the processor, the "balancing" function of the processor would similarly exclude data from the matched recording element on the contralateral array to ensure symmetry of data input for subsequent analysis.

The invention is not limited to the embodiment herein before described which may be varied in construction and detail without departing from the spirit of the invention. The entire teachings of any patents, patent applications or other publications referred to herein are incorporated by reference herein as if fully set forth herein.

The invention claimed is:

1. A method of detecting and/or transmitting subgaleal electrical signals, the method comprising the steps of:
    identifying an entry point on a head of a patient, for insertion of an array of linearly arranged electrodes;
    inserting a needle through a skin layer at the entry point to a subgaleal space;
    tunneling the needle through the subgaleal space to insert the array into the subgaleal space;
    wherein the array detects the subgaleal electrical signals and transmits the subgaleal electrical signals to a processor;
    identifying an exit point on the head;
    pulling or pushing the array so that an exit end of the array exits the head at the exit point;
    after the pulling or pushing step, attaching an exit stopper to the exit end of the array; and
    securing the exit stopper to the skin layer over the exit point to inhibit movement of the array.

2. The method of claim 1, wherein the tunneling the needle through the subgaleal space includes:
    tunneling approximately along a parasagittal anterior-posterior line overlying a first brain hemisphere of the patient.

3. The method of claim 2, wherein the parasagittal anterior-posterior line is a midpupillary line.

4. The method of claim 3, wherein the array is a first array, and the method further comprises:
    identifying a second entry point on the head, for insertion of a second array of linearly arranged electrodes;
    inserting the needle or a second needle through the skin layer at the second entry point to the subgaleal space; and
    tunneling the needle or the second needle through the subgaleal space to insert the second array approximately along a second parasagittal anterior-posterior line, wherein the second parasagittal anterior-posterior line is a midpupillary line overlying a second brain hemisphere of the patient.

5. The method of claim 4, the processor performing the steps of:
    monitoring the linearly arranged electrodes of the first array for an indication that an electrode of the first array is providing undesirable signal quality; and
    responsive to the monitoring, excluding a recording channel of the electrode of the first array providing the undesirable signal quality and excluding a recording channel of an electrode of the second array that is symmetrically placed relative to the electrode of the first array.

6. The method of claim 1, wherein the entry point is located at a parietal or frontal curvature of a skull of the patient.

7. The method of claim 1, wherein the method does not include an incision of the skin layer.

8. The method of claim 1, wherein general anesthesia is not administered to the patient prior to inserting the needle.

9. The method of claim 1, further comprising:
retaining the array in the subgaleal space via an entry stopper on an entry end of the array; and
securing the entry stopper to the skin layer over the entry point to inhibit movement of the array.

10. The method of claim 9, wherein the entry stopper has a disc-like shape and attaches to the entry end of the array.

11. The method of claim 1, wherein the exit stopper includes a disc-like portion and an opening to accommodate the array.

12. The method of claim 1, wherein the linearly arranged electrodes include a reference electrode, a ground electrode, and at least one recording electrode.

13. The method of claim 1,
wherein the linearly arranged electrodes include a reference electrode, a ground electrode, and at least one recording electrode,
wherein the exit point is located at a front of the head, and the entry point is located at a rear of the head, and
wherein the reference electrode and the ground electrode are further from the exit point than the at least one recording electrode is from the exit point.

14. A method of detecting and/or transmitting subgaleal electrical signals, the method comprising the steps of:
identifying a first entry point on a head of a patient, for insertion of a first array of linearly arranged electrodes, the first array of linearly arranged electrodes including a reference electrode, a ground electrode, and at least one recording electrode;
inserting a first needle through a skin layer at the first entry point to a subgaleal space and approximately along a first parasagittal anterior-posterior line overlying a first hemisphere of a brain of the patient, wherein the first parasagittal anterior-posterior line is a first midpupillary line;
tunneling the first needle through the subgaleal space to insert the first array into the subgaleal space;
wherein the first array detects first subgaleal electrical signals and transmits the first subgaleal electrical signals to a processor;
retaining the first array in the subgaleal space via a first entry stopper on an entry end of the first array;
securing the first entry stopper to the skin layer over the first entry point;
identifying a second entry point on the head, for insertion of a second array of linearly arranged electrodes;
inserting the first needle or a second needle through the skin layer at the second entry point to the subgaleal space and approximately along a second parasagittal anterior-posterior line overlying a second hemisphere of the brain of the patient, wherein the second parasagittal anterior-posterior line is a second midpupillary line;
tunneling the first needle or the second needle through the subgaleal space to insert the second array into the subgaleal space;
wherein the second array detects second subgaleal electrical signals and transmits the second subgaleal electrical signals to the processor;
identifying a first exit point on the head;
pulling or pushing the first array so that an exit end of the first array exits the head at the first exit point;
after the pulling or pushing step, attaching a first exit stopper to the exit end of the first array, wherein the first exit stopper includes a disc-like portion and an opening to accommodate the first array; and
securing the first exit stopper to the skin layer over the first exit point to inhibit movement of the first array.

15. The method of claim 14, wherein the method does not include an incision of the skin layer, and wherein general anesthesia is not administered to the patient prior to inserting the first needle or the second needle.

16. The method of claim 14, further comprising:
wherein the first entry stopper has a disc-like shape and attaches to the entry end of the first array.

17. The method of claim 16, further comprising:
retaining the second array in the subgaleal space via a second entry stopper on an entry end of the second array, wherein the second entry stopper has a disc-like shape and attaches to the entry end of the second array; and
securing the second entry stopper to the skin layer over the second entry point.

18. The method of claim 14, further comprising:
identifying a second exit point on the head;
pulling or pushing the second array so that an exit end of the second array exits the head at the second exit point;
after the pulling or pushing step the second array, attaching a second exit stopper to the exit end of the second array;
retaining the second array in the subgaleal space via the second exit stopper on the exit end of the second array, wherein the second exit stopper includes a disc-like portion and an opening to accommodate the second array; and
securing the second exit stopper to the skin layer over the second exit point to inhibit movement of the second array.

19. The method of claim 14,
wherein the first exit point is located at a front of the head, and the first entry point is located at a rear of the head, and
wherein the reference electrode and the ground electrode are further from the first exit point than the at least one recording electrode is from the first exit point.

20. A method of detecting and/or transmitting subgaleal electrical signals, the method comprising the steps of:
identifying an entry point on a head of a patient, for insertion of an array of linearly arranged electrodes, the identifying the entry point including using an insertion guide to identify the entry point for insertion of a needle in a parasagittal plane overlying a watershed zone between major vascular territories of frontal and parietal lobes;
inserting the needle through a skin layer at the entry point to a subgaleal space; and
tunneling the needle through the subgaleal space to insert the array into the subgaleal space;
wherein the array detects the subgaleal electrical signals and transmits the subgaleal electrical signals to a processor.

21. A method of detecting and/or transmitting subgaleal electrical signals, the method comprising the steps of:
identifying an entry point on a head of a patient, for insertion of a first array of linearly arranged electrodes;
inserting a needle through a skin layer at the entry point to a subgaleal space;

tunneling the needle through the subgaleal space to insert the first array into the subgaleal space;
wherein the first array detects the subgaleal electrical signals and transmits the subgaleal electrical signals to a processor;
identifying a second entry point on the head, for insertion of a second array of the linearly arranged electrodes;
inserting the needle or a second needle through the skin layer at the second entry point to the subgaleal space;
tunneling the needle or the second needle through the subgaleal space to insert the second array approximately along a second parasagittal anterior-posterior line, wherein the second parasagittal anterior-posterior line is a midpupillary line overlying a second brain hemisphere of the patient;
monitoring, by the processor, the linearly arranged electrodes of the first array for an indication that an electrode of the first array is providing undesirable signal quality; and
responsive to the monitoring, excluding, by the processor, a recording channel of the electrode of the first array providing the undesirable signal quality and excluding a recording channel of an electrode of the second array that is symmetrically placed relative to the electrode of the first array.

* * * * *

UNITED STATES PATENT AND TRADEMARK OFFICE
CERTIFICATE OF CORRECTION

| | |
|---|---|
| PATENT NO. | : 11,419,536 B2 |
| APPLICATION NO. | : 17/534854 |
| DATED | : August 23, 2022 |
| INVENTOR(S) | : Allen Waziri and Ronald G. Emerson |

It is certified that error appears in the above-identified patent and that said Letters Patent is hereby corrected as shown below:

On the Title Page

Item (63), delete "Continuation of application No. 17/236,932" and insert -- Continuation of application No. 17/236,982 --

Signed and Sealed this
Twenty-fifth Day of October, 2022

*Katherine Kelly Vidal*

Katherine Kelly Vidal
*Director of the United States Patent and Trademark Office*